(12) United States Patent  
Zhang et al.

(10) Patent No.: US 9,095,718 B2  
(45) Date of Patent: Aug. 4, 2015

(54) HEART-SOUNDS BASED ADAPTIVE CARDIAC RESYNCHRONIZATION THERAPY TIMING PARAMETER OPTIMIZATION SYSTEM

(71) Applicant: Medtronic, Inc., Minneapolis, MN (US)

(72) Inventors: Xusheng Zhang, Shoreview, MN (US); Paul J DeGroot, Shoreview, MN (US); Jeffrey M Gillberg, Coon Rapids, MN (US); Thomas J Mullen, Andover, MN (US); Aleksandre T Sambelashvili, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/856,152

(22) Filed: Apr. 3, 2013

(65) Prior Publication Data

US 2013/0268017 A1    Oct. 10, 2013

Related U.S. Application Data

(60) Provisional application No. 61/620,277, filed on Apr. 4, 2012.

(51) Int. Cl.
| | |
|---|---|
| A61N 1/36 | (2006.01) |
| A61N 1/365 | (2006.01) |
| A61N 1/362 | (2006.01) |
| A61N 1/368 | (2006.01) |

(52) U.S. Cl.  
CPC .......... *A61N 1/36585* (2013.01); *A61N 1/3627* (2013.01); *A61N 1/3682* (2013.01); *A61N 1/3684* (2013.01)

(58) Field of Classification Search  
None  
See application file for complete search history.

(56) References Cited

U.S. PATENT DOCUMENTS

| | | | |
|---|---|---|---|
| 5,554,177 | A | 9/1996 | Kieval et al. |
| 5,683,432 | A | 11/1997 | Goedeke et al. |
| 6,418,346 | B1 | 7/2002 | Nelson et al. |
| 6,442,433 | B1 | 8/2002 | Linberg |

(Continued)

FOREIGN PATENT DOCUMENTS

| | | |
|---|---|---|
| WO | WO 2004/060483 A1 | 7/2004 |
| WO | WO 2012/058521 A1 | 5/2012 |

OTHER PUBLICATIONS (PCT/US2013/035233) PCT Notification of Transmittal of the International Search Report and the Written Opinion of the International Searching Authority.

*Primary Examiner* — Brian T Gedeon  
*Assistant Examiner* — Ankit Tejani  
(74) *Attorney, Agent, or Firm* — Carol F. Barry

(57) ABSTRACT

A medical device and associated method for controlling a cardiac pacing therapy sense a first cardiac signal including events corresponding to cardiac electrical events and a second cardiac signal including events corresponding to cardiac hemodynamic events. A processor is enabled to measure a cardiac conduction time interval using the first cardiac signal and control a signal generator to deliver a pacing therapy. A pacing control parameter is adjusted to a plurality of settings during the pacing therapy delivery. A hemodynamic parameter value is measured from the second cardiac signal during application of each of the control parameter settings. The processor identifies an optimal setting from the plurality of settings and solves for a patient-specific equation defining the pacing control parameter as a function of the cardiac conduction time interval.

32 Claims, 7 Drawing Sheets

(56) References Cited

U.S. PATENT DOCUMENTS

| | | | |
|---|---|---|---|
| 6,480,745 B2 | 11/2002 | Nelson et al. | |
| 6,599,250 B2 | 7/2003 | Webb et al. | |
| 7,079,896 B1 | 7/2006 | Park et al. | |
| 7,181,284 B2 | 2/2007 | Burnes et al. | |
| 7,209,786 B2 * | 4/2007 | Brockway et al. | 607/17 |
| 7,254,442 B2 | 8/2007 | Ven Gelder et al. | |
| 7,260,429 B2 | 8/2007 | Siejko et al. | |
| 7,548,784 B2 | 6/2009 | Chinchoy | |
| 7,615,012 B2 | 11/2009 | Von Arx et al. | |
| 7,676,264 B1 * | 3/2010 | Pillai et al. | 607/9 |
| 7,689,283 B1 | 3/2010 | Schecter | |
| 7,706,879 B2 | 4/2010 | Burnes et al. | |
| 7,844,334 B2 | 11/2010 | Maile et al. | |
| 7,883,470 B2 | 2/2011 | Scheiner et al. | |
| 2007/0129764 A1 | 6/2007 | Burnes | |
| 2008/0103406 A1 | 5/2008 | Kameli | |
| 2008/0177344 A1 | 7/2008 | Maskara et al. | |
| 2008/0195168 A1 | 8/2008 | Arand et al. | |
| 2008/0294214 A1 | 11/2008 | Holmstrom et al. | |
| 2009/0192561 A1 | 7/2009 | Bauer | |
| 2009/0254139 A1 | 10/2009 | Bjorling | |
| 2010/0023078 A1 | 1/2010 | Dong et al. | |
| 2010/0121401 A1 | 5/2010 | Min et al. | |
| 2010/0145405 A1 | 6/2010 | Min et al. | |

* cited by examiner

HEART-SOUNDS BASED ADAPTIVE CARDIAC RESYNCHRONIZATION THERAPY TIMING PARAMETER OPTIMIZATION SYSTEM

CROSS-REFERENCE TO RELATED APPLICATIONS

This application claims the benefit of U.S. Provisional Application No. 61/620,277, filed on Apr. 4, 2012. The disclosure of the above application is incorporated herein by reference in its entirety.

FIELD OF THE DISCLOSURE

The disclosure relates generally to medical devices and, in particular, to a medical device and associated method for controlling cardiac resynchronization therapy.

BACKGROUND

Cardiac resynchronization therapy (CRT) is a treatment for heart failure patients in which one or more heart chambers are electrically stimulated (paced) to restore or improve heart chamber synchrony. Improved heart chamber synchrony is expected to improve hemodynamic performance of the heart, such as measured by ventricular pressure and the rate of change in ventricular pressure or other hemodynamic measures. Achieving a positive clinical benefit from CRT is dependent on several therapy control parameters, such as the atrioventricular (AV) delay and the ventricular-ventricular (VV) delay. The AV delay controls the timing of ventricular pacing pulses relative to an atrial depolarization, intrinsic or paced. The ventricular-ventricular (VV) delay controls the timing of a pacing pulse in one ventricle relative to a paced or intrinsic sensed event in the other ventricle.

Numerous methods for selecting optimal AV and VV delays for use in controlling CRT pacing pulses have been proposed. For example, clinicians may select an optimal AV or VV delay using Doppler echocardiography. Such clinical techniques are time-consuming and require an expert technician to perform. A need remains for optimizing CRT control parameters to achieve a positive result.

SUMMARY

A medical device and associated method control the delivery of CRT. The techniques disclosed herein provide updatable equations for computing an optimized CRT control parameter as a function of a measured cardiac conduction time. In some embodiments, a coefficients and/or intercept of a patient-specific optimized equation for computing a control parameter as a function of a measured cardiac conduction time are stored in the memory of an implantable medical device and used by a processor to compute an updated control parameter setting. Each time the cardiac conduction time is measured, the stored equation can be used by the processor to update a corresponding control parameter. Instead of a using fixed equations and updating CRT control parameters only in response to new measurements of cardiac conduction times, the equation itself can also be updated. The equation is updated by solving for a coefficient and/or intercept used in the equation when a hemodynamically optimized control parameter value and a conduction time measurement are known. The control parameter value may be optimized based on hemodynamic parameter values derived from a heart sound signal in some embodiments. Once the control parameter value resulting in the greatest improvement in a hemodynamic parameter value is identified, a related cardiac conduction time can be measured and a coefficient or intercept is solved for and stored to define a patient-specific equation for computing an optimized CRT control parameter value. In various embodiments, the control parameter is an AV or a VV delay and the equation for computing the AV or VV delay is a linear function of a cardiac conduction time interval. Examples of a cardiac conduction time interval include an AV conduction time interval, a P-wave duration, or a QRS duration.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In "adaptive CRT", pacing pulses are selectively delivered in both the right and left ventricle (biventricular pacing) or only in the left ventricle (LV-only pacing or single ventricle pacing). The pacing device is configured to switch between biventricular pacing and single ventricle LV-only pacing based on measurements of atrial-to-ventricular (AV) conduction time intervals, i.e. the time for an atrial depolarization to conduct to the ventricles and cause a ventricular depolarization. When AV conduction is impaired, i.e. blocked or slowed, biventricular pacing is delivered. When AV conduction occurs within an expected "normal" time interval, LV-only pacing is delivered to allow intrinsic AV conduction to occur and improve ventricular synchrony through the LV-only pacing. During either biventricular or single ventricle LV-only pacing, the atrial chambers may or may not be paced.

A CRT control parameter value, such as an AV delay, selected for controlling biventricular pacing may not necessarily be the optimal control parameter value for controlling LV-only pacing. Furthermore, CRT control parameters that are set based on clinical results obtained from a population of patients may not be optimal for an individual patient. Optimization of CRT control parameters for patients individually can be time-consuming and require considerable technical expertise. A system and associated method for controlling CRT therapy delivery parameters during adaptive CRT is described herein for providing patient-specific optimized CRT control parameters during both biventricular and LV-only pacing modes, without requiring hemodynamic measurements every time the control parameter is adjusted. For descriptions of methods and devices that may be implemented for delivering adaptive CRT, reference is made to U.S. Pat. No. 7,254,442 (van Gelder et al.), U.S. Pat. No. 7,181,284 (Burnes, et al.), and U.S. Pat. No. 7,706,879 (Burnes, et al.), all of which patents are hereby incorporated herein by reference in their entirety. Another example of a device for delivering CRT in which techniques disclosed herein could be implemented is generally disclosed in U.S. Publication No. 2008/0177344 (Maskara et al.).

Figure 1:
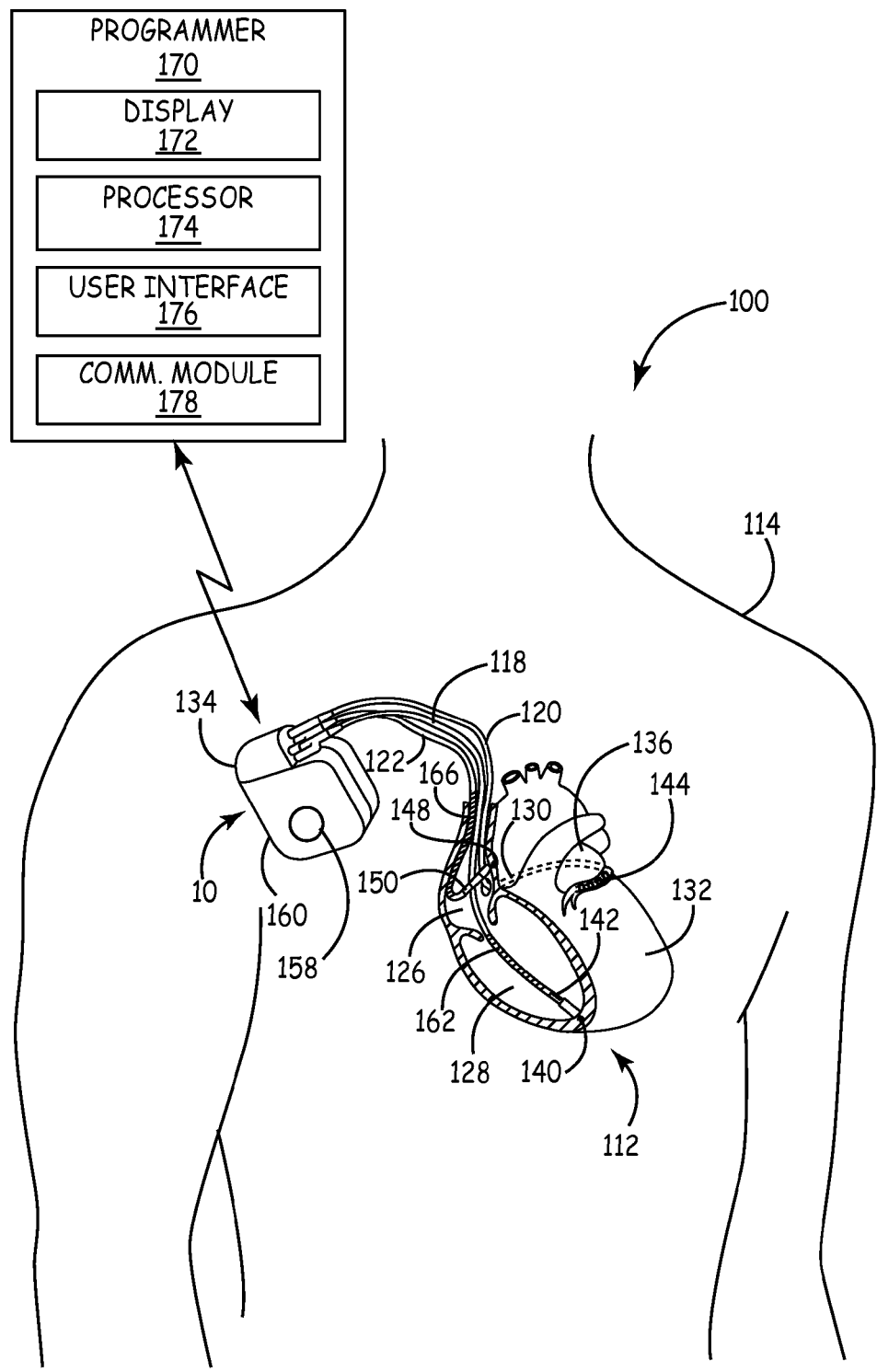
FIG. 1 is a schematic diagram of one embodiment of an implantable medical device (IMD) system in which techniques disclosed herein may be implemented to provide therapy to a patient's heart.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering at least biventricular and LV-only pacing, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver cardioversion or defibrillation therapy to heart 112 in the form of electrical shock pulses. While IMD 10 is shown in a right pectoral implant position in FIG. 1, a more typical implant position, particularly when IMD 10 is embodied as an ICD, is a left pectoral implant position.

IMD 10 includes internal circuitry for performing the functions attributed to IMD 10, and a housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT therapy, which includes the use of a selected pacing vector for LV pacing that utilizes at least one electrode 144 on multipolar LV lead 120. IMD 10 is configured to pace in one or both ventricles 128 and 132 for controlling and improving ventricular synchrony. The methods described herein are implemented in a dual or multi-chamber pacemaker or ICD delivering pacing pulses to the right and left ventricles using programmable pacing pulse timing parameters and selected pacing vectors. In particular, IMD 10 is configured to provide "adaptive CRT" which automatically switches between biventricular pacing and LV-only pacing in response to changes in the patient's intrinsic AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 may request IMD 10 to perform a CRT optimization algorithm and transmit results to programmer 170 or request data stored by IMD 10 relating to CRT optimization procedures performed automatically by IMD 10 on a periodic basis. In some embodiments, signal data acquired by IMD 10 may be transmitted to programmer 170, and programmer 170 performs the CRT optimization algorithm using the transmitted signals to establish patient-specific optimized equations for computing CRT control parameters. The resulting equations, or the coefficient(s) and intercept(s) defining an equation for computing a CRT control parameter, would then be transmitted back to the IMD 10.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review heart sound data and CRT optimization results and authorize programming of IMD pacing control parameters. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

Figure 2:
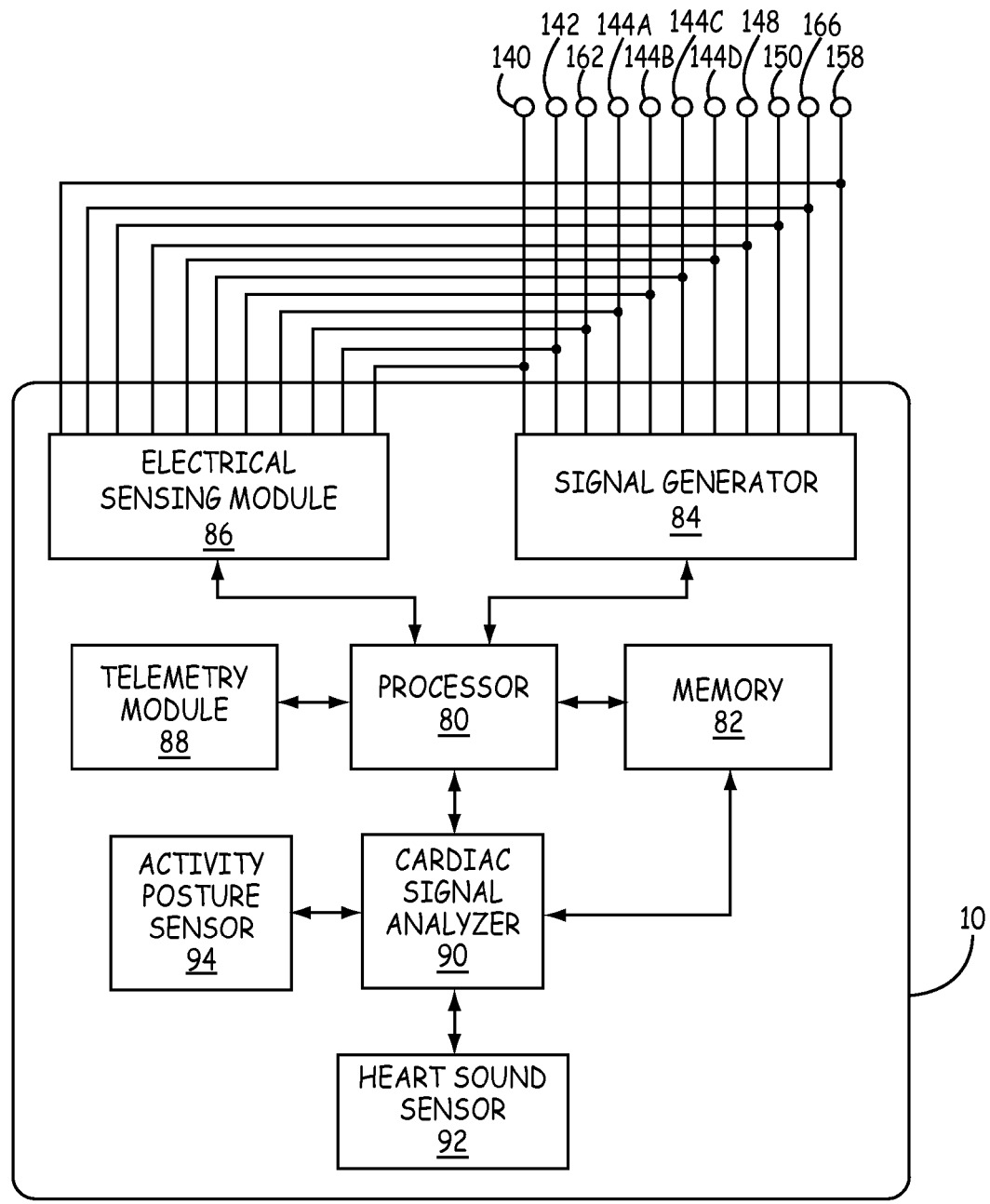
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, also referred to herein as "processor" 80, memory 82, signal generator 84, sensing module 86, and telemetry module 88. IMD 10 further includes cardiac signal analyzer 90, heart sound sensor 92 and activity/posture sensor 94.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to AV and/or VV delays during CRT. These delays are set based on an analysis of cardiac signals by analyzer 90 as will be described herein.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112. Sensing module 86 may further include digital signal processing circuitry for providing processor 80 or cardiac signal analyzer 90 with digitized EGM signals.

The occurrence of R-waves in the ventricles, e.g. in the RV, is used in monitoring intrinsic AV conduction time. In particular, prolongation of the AV conduction time or the detection of AV block based on R-wave sensing during no ventricular pacing (or pacing at an extended AV delay that allows intrinsic conduction to take place) is used to control adaptive CRT. When AV conduction is impaired, signal generator 84 is controlled by processor 80 to deliver biventricular pacing, i.e. pacing pulses are delivered in the RV and the LV using a selected AV delay and a selected VV delay. When AV conduction is intact, signal generator 84 is controlled by processor 80 to deliver LV-only pacing at a selected AV delay to improve ventricular synchrony.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber. Memory 82 stores equations established for computing optimal CRT timing control parameters such as AV and VV delays. The equations may be stored in the form of coefficient and intercept values defining a function of a cardiac conduction time interval that is used for computing an optimal CRT timing control parameter as will be described in greater detail below.

Cardiac signal analyzer 90 receives signals from heart sound sensor 92 for determining heart sound-based hemodynamic metrics used to identify optimal CRT control parameters. As used herein, the term "hemodynamic" pertains to the movements involved in the circulation of blood including movements of the heart in pumping blood such as heart valve opening and closure and cardiac wall motion. In alternative embodiments, a different physiological sensor may be used in addition to or substituted for heart sound sensor 92 for providing cardiac signal analyzer 90 with a cardiac signal correlated to hemodynamic function, particularly ventricular function. Alternative sensors may be embodied as a mechanical, optical or other type of transducer, such as a pressure sensor, oxygen sensor or any other sensor that is responsive to cardiac function and produces a signal corresponding to cardiac mechanical function or an indication correlated to ventricular synchrony. Analysis of the signal is used in guiding selection of AV and VV delays used to control CRT pacing pulses. Cardiac signal analyzer 90 may provide additional EGM signal analysis capabilities using signals from sensing module 86.

Heart sound sensor 92 generates an electrical signal in response to sounds or vibrations produced by heart 112. Sensor 92 may be implemented as a piezoelectric sensor, a microphone, an accelerometer or other type of acoustic sensor. In some examples, heart sound sensor 92 may be used as both an acoustic to electrical transducer and as an electrical to acoustic transducer. In such examples, the sensor may also be used to generate an audible alarm for the patient, such as a buzzing or beeping noise. The alarm may be provided in response to detecting a hemodynamic metric that crosses an alarm threshold.

In FIG. 2, heart sound sensor 92 is enclosed within housing 160 of IMD 10 with other electronic circuitry. In other examples, heart sound sensor 92 may be formed integrally with or on an outer surface of housing 160 or connector block 134. In still other examples, heart sound sensor 92 is carried by a lead 118, 120, 122 or another lead coupled to IMD 10. In some embodiments, heart sound sensor 92 may be implemented as a remote sensor that communicates wirelessly with IMD 10. In any of these examples, sensor 92 is electrically or wirelessly coupled to cardiac signal analyzer 90 to provide a signal correlated to sounds generated by heart 112 for deriving hemodynamic function metrics.

Figure 3:
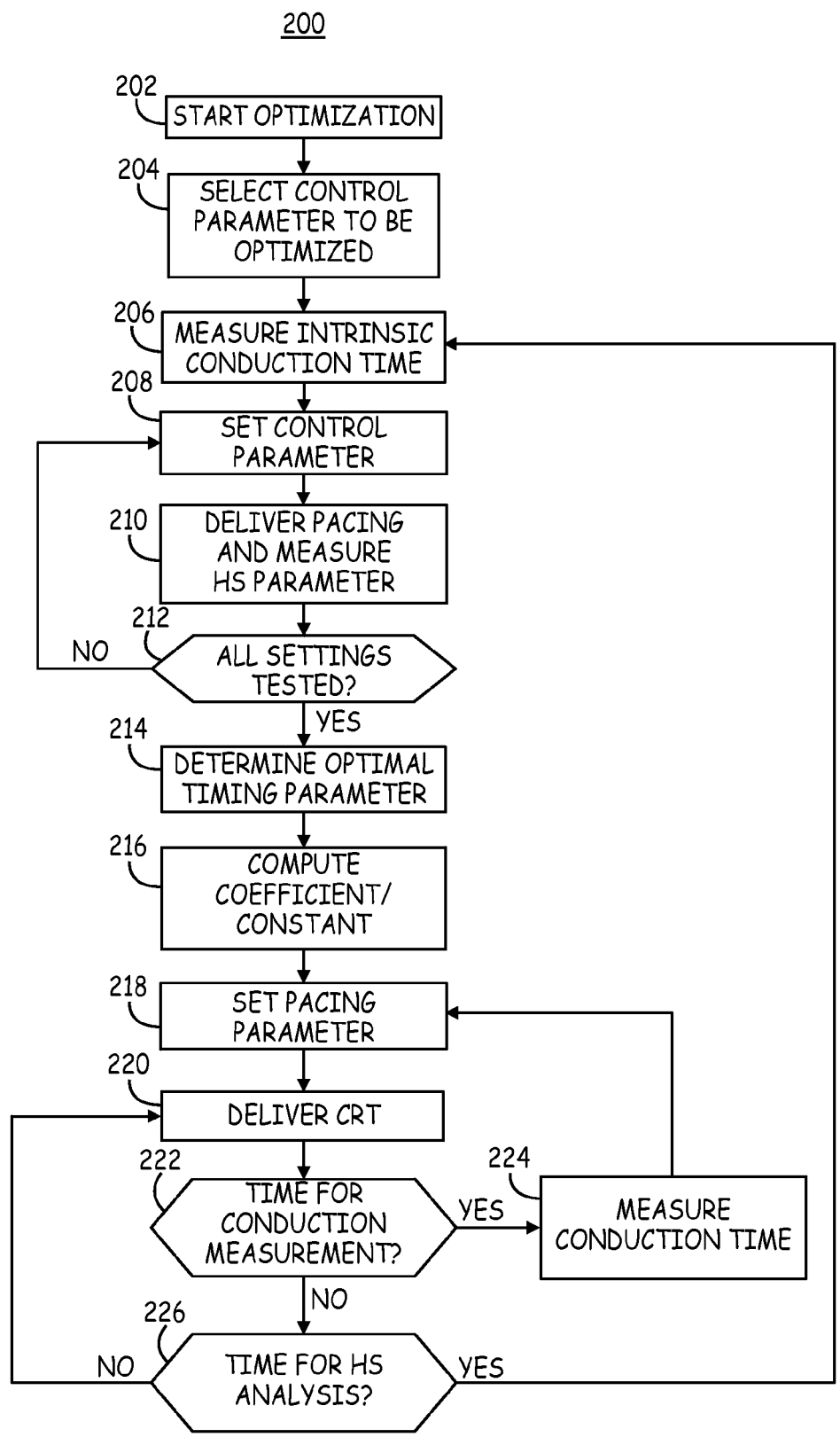
FIG. 3 is a flow chart of a method for controlling CRT according to one embodiment.

FIG. 3 is a flow chart 200 of a method for controlling CRT according to one embodiment. Flow chart 200 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a non-transitory computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like with the sole exception being a transitory, propagating signal. The instructions may be implemented as one or more software modules, which may be executed by themselves or in combination with other software.

At block 202, the CRT optimization process is initiated. The process may be initiated manually by a clinician or other user interacting with programmer 170. The process may additionally or alternatively be initiated on a regular periodic basis or in response to a monitored heart rate or hemodynamic metric indicating a worsening in cardiac function. Initially, heart sound signals are used to identify optimal pacing control parameter settings during the optimization process. This initial process of identifying optimal settings may be performed at the time of IMD implantation or during an office visit under the supervision of a clinician. The initial process may be performed while the patient is at rest, e.g. in a sitting or lying position, or other controlled conditions.

If the process is being initiated automatically, e.g. on a periodic basis, the IMD processor may use other sensing input to establish desired conditions for the process to take place. For example, a heart rate determined from signals from electrical sensing module 86, the posture sensor or activity sensor 94, a respiration rate, level of signal noise or artifacts on a sensor signal due to patient activity, or any combination thereof, may be used to confirm a resting state or other desired state for performing the optimization procedure. It is recognized that the process described is not necessarily always performed during a resting state but may desirably be performed during various levels of activity or heart rates for determining optimal CRT control parameters at different heart rates and/or activities.

Once the process is initiated, the CRT control parameter being optimized is selected at block 204. For example, the process illustrated by flow chart 200 may be implemented to optimize an AV delay for use during LV-only pacing and an AV delay and a VV delay for use during biventricular pacing. A single parameter may be optimized using the process described here or multiple parameters may be optimized in a sequential manner. The parameter selected at block 204 may depend in part on the status of AV conduction and the biventricular or LV pacing mode selected at the time the process is being performed.

An intrinsic conduction time interval is measured at block 206 based on the pacing parameter selected to be optimized at block 204. An intrinsic conduction time interval can refer to the time interval a conducted event occurs after either a paced or sensed intrinsic event. For example, an AV conduction time interval may be measured from an atrial pacing pulse to the intrinsically conducted RV R-wave (Apace-RVsense interval) or from an intrinsic atrial sensed P-wave to the intrinsically conducted RV R-wave (Asense-RVsense interval). The Apace-RVsense interval and Asense-RVsense interval can be referred to collectively as the A-RVsense interval, though it is recognized that each may be measured separately to provide for computation of different CRT control parameter settings under conditions of atrial pacing and under conditions of atrial sensing. In one example, if the AV delay for use during LV-only pacing is being optimized, the A-RVsense interval is measured. The A-RVsense interval is a conduction time interval used in setting an AV delay to control delivery of LV pacing pulses during LV-only pacing.

In another example, the conduction time interval measured at block 206 is the P-wave duration measured as the interval between the time a P-wave is first sensed (or an atrial pacing pulse) to the end of the P-wave. The P-wave duration, also referred to herein as "A-Pend", can be used in computing an AV delay, e.g. during biventricular pacing as will be further described below. In yet another example, the width or duration of a QRS signal is measured as the conduction time interval at block 206. The QRS signal width may be used to compute a VV delay for controlling biventricular pacing.

Once a cardiac conduction time interval is measured at block 206, that value is stored or may be updated at a later time for use in setting a CRT control parameter. During the initial phase of the optimization process, a first test setting is selected for the control parameter being optimized at block 208. The first test setting for the control parameter may be a default or nominal value, or a most recently programmed value. Pacing is delivered using the test control parameter setting at block 210. For example, LV-only pacing may be delivered using a test AV delay setting. In other cases, biventricular pacing may be delivered using a test AV delay setting or a test VV delay setting.

At block 210, a signal generated by heart sound sensor 92 is received and analyzed by cardiac signal analyzer 90. One or more heart sound (HS) parameters are derived from the signal as hemodynamic indicators of cardiac function. The HS parameters measured at block 210 are stored for multiple test settings of the CRT control parameter being optimized. If not all settings have been tested, as determined at block 212, the process returns to block 208 to adjust the control parameter setting and measure corresponding HS parameter values during CRT delivery using the test setting.

After determining and storing HS parameter values for each test setting, the optimal setting is identified at block 214 based on comparisons of the HS parameter values. Numerous HS parameter values may be derived from the HS sensor signal by cardiac signal analyzer 90 which are correlated to ventricular systolic and/or diastolic function. In one embodiment, an S1-S2 time interval is measured as an indication of ventricular ejection time. The control parameter setting resulting in maximum S1-S2 time interval is determined as an optimal setting such that ejection time is maximized. In another example, the QRS-S1 time interval is measured as a ventricular pre-ejection interval. The control parameter setting resulting in a minimum QRS-S1 time interval is determined as the optimal parameter setting in one embodiment.

In still another example, a myocardial performance index (MPI) is determined as the HS parameter by measuring the width of the S1 sound, the width of the S2 sound, and the S1-S2 interval. The MPI is then computed as MPI=(S1width+S2width)/(S1-S2 interval). Any one or combination of the above-mentioned HS parameters may be used in identifying an optimal control parameter setting. In particular, the above-mentioned parameters are useful in determining an optimal AV delay setting used during LV-only pacing or a VV delay setting during biventricular pacing for improving ventricular synchrony.

During biventricular and during LV-only pacing, HS parameters can also be used in identifying optimal control parameter settings for improving atrial-ventricular synchrony. For example, an S3-S4 time interval may be determined as an indicator of ventricular filling time. A pacing control parameter resulting in a maximum S3-S4 interval may be identified as an optimal parameter yielding maximum ventricular filling. Varying the AV delay during biventricular pacing or LV-only pacing enables the processor to identify the AV delay setting resulting in minimum truncation of the active filling phase, and thus maximized ventricular filling.

Other HS parameters may be derived from the HS sensor signal as indicators of hemodynamic function and/or heart chamber synchrony. Any combination of HS parameters may be determined and used in identifying an optimal setting for a CRT control parameter or combination of control parameters. The HS parameters may be determined from measurements of the HS signal over one or more cardiac cycles. HS parameters may be measured from a raw filtered HS sensor signal or after determining an ensemble averaged HS signal. HS parameter values may be compared directly to each other, to a target value or range of the HS parameter, which may be a patient specific target value or range or based on data from a patient population.

Knowing the optimal control parameter setting and the previously measured conduction time interval (from block 206), a coefficient used in computing the control parameter setting during CRT operation are computed at block 216. For instance, in case of a linear relationship between the optimal control parameter and the measured conduction time interval, an equation used to automatically adjust a CRT timing parameter can be generally expressed as:

$$Y=K*X+C$$

wherein Y is the timing parameter setting, K is a coefficient, X is a measured conduction time interval, and C is an intercept. In some embodiments, K may be 1 or C may be zero simplifying the equation to Y=X+C or Y=K*X, respectively. Using one or more HS parameters measured for each test setting, the optimal value for Y out of multiple test settings is identified as described above. Having previously measured X (the conduction time) at block 206, K can be solved for when C is set to a constant (or 0). Alternatively, C can be solved for when K is set to a constant (or 1). In this way, the coefficient K or intercept C used in an equation to compute a CRT timing control parameter Y as a function of a measured intrinsic conduction time X is customized to the patient's own hemodynamic performance based on HS signal analysis. The patient-specific optimized coefficient or intercept is stored in IMD memory to enable a new control parameter to be computed whenever the conduction time interval is re-measured.

At block 218, the pacing control parameter being optimized is set to the optimum value determined based on the HS signal analyses. CRT is delivered using the optimized control parameter at block 220. Periodically, a conduction time measurement is updated to enable updating or adjustment of an associated control parameter as needed. If it is time to update a conduction time interval measurement, as determined at block 222, the conduction time interval is measured at block 224. The conduction time interval may be measured at regular intervals, which may be on the order of every few seconds, minutes, hours, daily, weekly or other selected interval.

After measuring the conduction time interval at block 224, the associated pacing control parameter is updated at block 218 using the updated conduction time measurement and the stored coefficient or intercept determined at block 216. In this way, a timing control parameter is dynamically adjusted in response to changes in intrinsic conduction time using a patient-specific, hemodynamically-optimized relationship between the measured conduction time and the timing control parameter.

In addition to periodically updating the conduction time interval measurement, the HS analysis may be repeated to update the value of a stored coefficient or intercept used to compute the optimal pacing control parameter. HS analysis may be scheduled to occur at regular intervals, for example daily, weekly, or monthly. If it is time to repeat the HS analysis, as determined at block 226, the process returns to block 206 to measure the conduction time interval used to compute the pacing control parameter. At blocks 208 through 212, the control parameter setting is varied until HS parameter measurements are obtained for all desired test settings.

As described above, the optimal pacing parameter setting is identified based on HS parameter measurement comparisons at block 214. An updated coefficient or intercept is solved for using the optimal parameter setting and a currently measured conduction time interval. The updated coefficient or intercept defining the control parameter as a function of the measured conduction time is stored at block 216. In this way, both the conduction time interval and the equation (i.e. the coefficient or intercept values) used to compute an optimal control parameter setting are adaptively updated to patient-specific values as needed throughout CRT delivery. The conduction time interval may be updated more frequently to enable CRT control parameters to be optimized as the patient conduction status changes. The hemodynamic optimization may be performed less frequently than conduction time measurements to enable optimized equations for computing CRT control parameters to be updated as the mechanical function of the heart changes.

Figure 4:
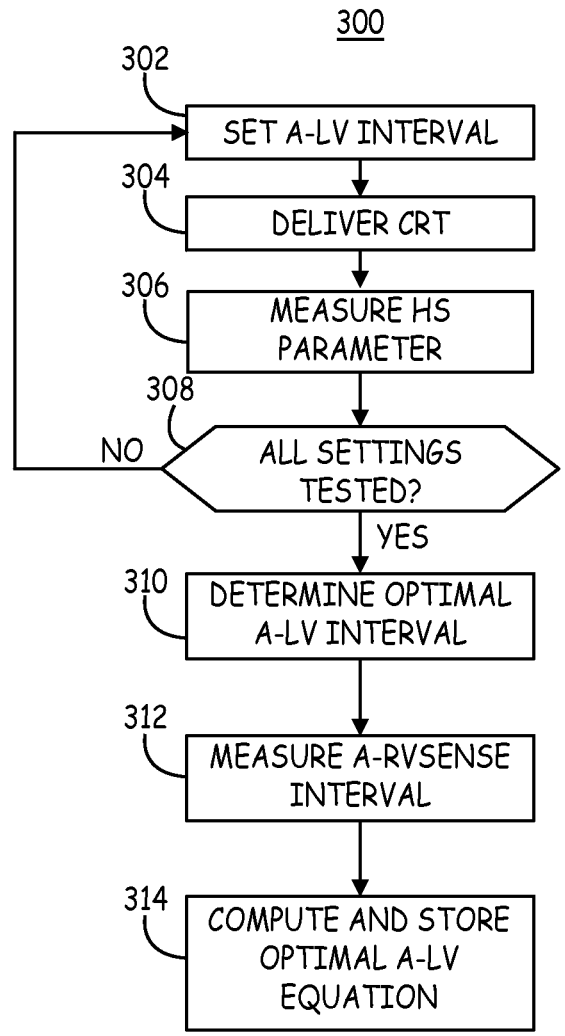
FIG. 4 is a flow chart of a method for establishing an optimized AV delay used during LV-only pacing according to one embodiment.

FIG. 4 is a flow chart 300 of one method for establishing an optimized AV delay used during LV-only pacing. At block 302, an initial A-LV delay is set. The process shown in flow chart 300 may be implemented during atrial pacing or during atrial sensing. The process may be intentionally performed during both pacing and sensing to obtain a unique equation for computing the optimal Apace-LV delay during periods of atrial pacing and the optimal Asense-LV delay for use during periods of atrial sensing. Furthermore, the process may be performed at different intrinsic and/or paced heart rates. A sensed heart rate may be used to trigger the process to occur during different heart rate ranges or levels. As such, the process shown by flow chart 300 may be performed to obtain all the necessary coefficients or intercepts used to compute different A-LV delay settings for use during atrial pacing at one or more heart rate ranges and during atrial sensing at one or more heart rate ranges.

At block 304, CRT is delivered using the test A-LV delay set at block 302. One or more HS parameters are measured at block 306. After collecting HS parameter measurements for at least two different A-LV delay test settings, as determined at block 308, the optimal A-LV delay is identified at block 310 through HS parameter value comparison. As described above, in some embodiments a maximized ejection interval, minimized pre-ejection interval, or maximized myocardial performance index derived from HS signal analysis may be used to indicate the optimal A-LV delay.

At block 312, an A-RVsense conduction time interval is measured. In one embodiment, the A-LV delay is computed as a function of the A-RVsense conduction time interval. For example, A-LV delay may be computed as A-LV delay=K*(A-RVsense)+C. C is stored as a constant that may be programmed to a selected positive or negative value. In one embodiment, C may be 45, 30, 20 or −65 ms. The optimal value of C may be based on clinical studies of a population of patients. For example, modeling of optimal control parameters may be performed using measured conduction times and hemodynamic metrics from a population of patients for determining an optimal value for C.

Knowing the optimal A-LV delay based on HS signal analysis, the optimal coefficient K can be solved for using the measured A-RV sense interval and fixed value for C. At block 314, the value of K is stored and subsequently used to compute an updated A-LV delay each time the A-RVsense interval is measured.

Alternatively, a fixed value of K may be used in the equation A-LVdelay=K*(A-RVsense)+C. In this case, C is a HS-based optimized value. The value of C is solved for using an optimized A-LV delay, a measured A-RVsense interval, and a fixed value of K. C may be considered, in this embodiment, as a pre-ejection interval or PEI, in that it will control how much earlier (or later) the LV is paced relative to the RV sense. During CRT delivery, an optimized value of the A-LV delay setting can be updated by computing the A-LV delay from the equation defined by the stored value of C and fixed value of K and updated measurements of A-RVsense. Periodically the value of C is adjusted based on a HS-based optimization of the A-LV delay.

In yet another embodiment, both K and C may be determined based on HS-based optimization at two different points in time. In this case, K and C are solutions of a set of two equations for the two time points: A-LVdelay$_1$=K*(A-RVsense$_1$)+C, A-LVdelay$_2$=K*(A-RVsense$_2$)+C. During CRT delivery, A-LV delay is calculated from the periodic measurements of A-RVsense and coefficients K and C. Coefficient K and intercept C can be periodically adjusted based on HS-based optimization of the A-LV delay. At some times, K is held constant at the previously optimized value to enable optimization of C. At other times, C is held constant at the previously optimized value to enable optimization of K.

In the illustrated embodiment, A-LV delay is defined as a linear function of the A-RVsense interval. It is recognized that non-linear functions could also be defined for computing and setting a pacing timing control interval. The equation for computing the control parameter value is a function of a measured intrinsic conduction time. Updatable values for intercepts or coefficients included in the defining equation are updated and stored based on HS optimization of the timing parameter. Furthermore, while the A-LV delay is determined as a function of the A-RV sense interval, a different conduction time could be substituted in the above equation. For example, the A-LV delay could be defined as a function of P-wave duration in some embodiments.

Figure 5:
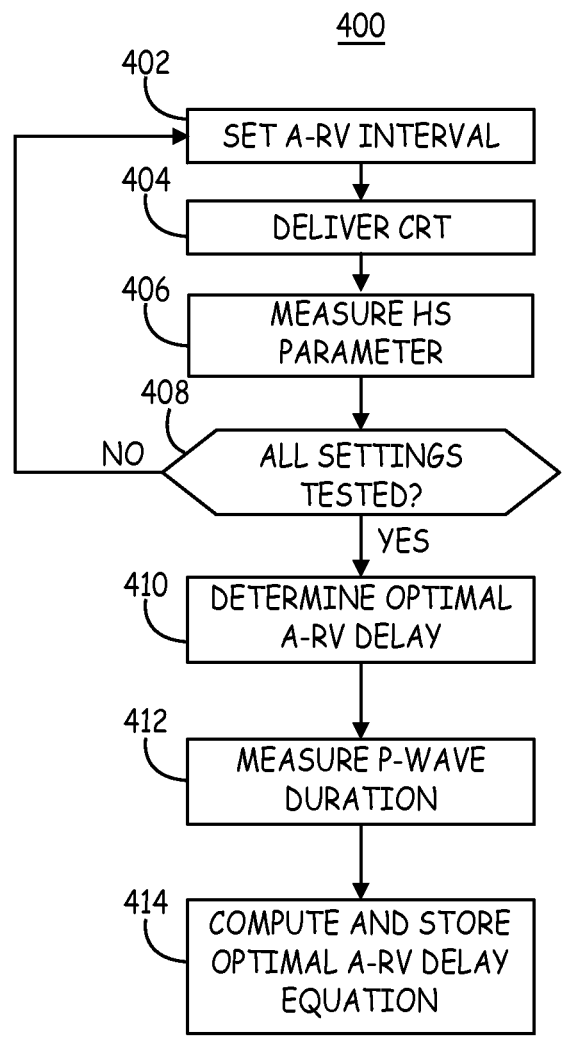
FIG. 5 is a flow chart of a method for setting an optimal AV delay during biventricular pacing according to one embodiment.

FIG. 5 is a flow chart 400 of a method for setting an optimal AV delay during biventricular pacing. In one example, the AV delay used during biventricular pacing controls timing of the RV pacing pulse relative to an atrial paced or sensed event and is therefore referred to as an A-RV delay. The LV pacing pulse may then be controlled by a VV delay that may be 0 ms (simultaneous RV and LV pacing), a positive value (resulting in LV pacing before the RV pacing pulse) or, according to one convention, a negative value (resulting in an LV pacing pulse later than the RV pacing pulse). It is recognized that other conventions may be used for defining when both the RV and the LV pacing pulses are delivered. In another example, an A-RV delay and an A-LV delay are each set to control the timing of the RV and LV pacing pulses, respectively, relative to each other and relative to the atrial activation. In still other conventions, an A-LV delay may be used to control timing of the LV pacing pulse, and the RV pacing pulses are delivered at the expiration of a VV delay to control the relative timing of the RV pacing pulse to the LV pacing pulse. The disclosed techniques of determining an optimal pacing timing control interval using heart sound analysis and then solving for an optimal coefficient or intercept in an equation defining the pacing timing control interval as a function of a measured intrinsic conduction time following a paced or sensed event is generally applicable to any of these conventions.

In the illustrative embodiment of FIG. 5, an initial A-RV delay is set at block 402. CRT is delivered in a biventricular pacing mode at block 404 using the initial A-RV delay. During optimization of the A-RV delay, a nominal VV delay setting may be used, e.g. a VV delay of 0 ms to provide simultaneous ventricular pacing while the AV delay is being optimized. A HS parameter is measured at block 406 for the initial A-RV delay setting. The A-RV delay is adjusted to one or more additional test settings at block 402 until a HS parameter has been measured for multiple test settings as determined at decision block 408.

The HS parameter measured at block 406 may be a parameter correlated to diastolic function, e.g. truncation of the A-wave based on a HS signal-derived surrogate, S1 amplitude or S3-S4 interval or amplitudes of S3 or S4. Based on the HS parameter values measured and stored at block 406, an optimal A-RV delay is identified at block 410 as, for example, the shortest A-RV delay resulting in no truncation of the A-wave, or the A-RV delay resulting in maximum S1 amplitude or maximum S3-S4 interval. Alternatively, the A-RV delay may be optimized based on a systolic function parameter.

The HS parameter measured may include an S1-S2 interval, an interval from a ventricular pacing pulse to S2, or an interval from an RV sense to S2. The optimal A-RV delay may be identified as a maximized S1-S2 interval or a delay resulting in a sudden change in the interval from an RV sensed or paced event to the S2 sound The A-RV delay will be computed as a function of a measured conduction time using an equation defined based on the HS signal analysis. The conduction time interval is measured at block 412. In one embodiment, a P-wave duration is measured at block 412. The P-wave duration may be measured from the time of a P-wave sensing threshold crossing (or pacing pulse) to an end of P-wave detection, e.g. a second threshold crossing which may be a negative-going crossing. The A-RV delay may be defined as the intrinsic P-wave duration plus an offset (i.e. intercept). The offset may be solved for knowing the optimal A-RV delay and the measured P-wave duration at block 414. The optimal offset is stored and is later used to compute an optimal A-RV delay whenever the P-wave duration measurement is updated. In one embodiment, the P-wave duration is measured every 12-24 hours, e.g. every 16 hours, and a new A-RV delay is computed using the stored offset. The optimal offset is also updatable using periodic HS signal analysis. The offset may be updated less frequently than the P-wave duration measurement. The offset may be updated using the HS signal analysis technique, for example once a week.

It is recognized that in alternative embodiments, other cardiac conduction intervals may be measured for use in computing A-RV delay such as an intrinsic A-RVsense interval.

Figure 6:
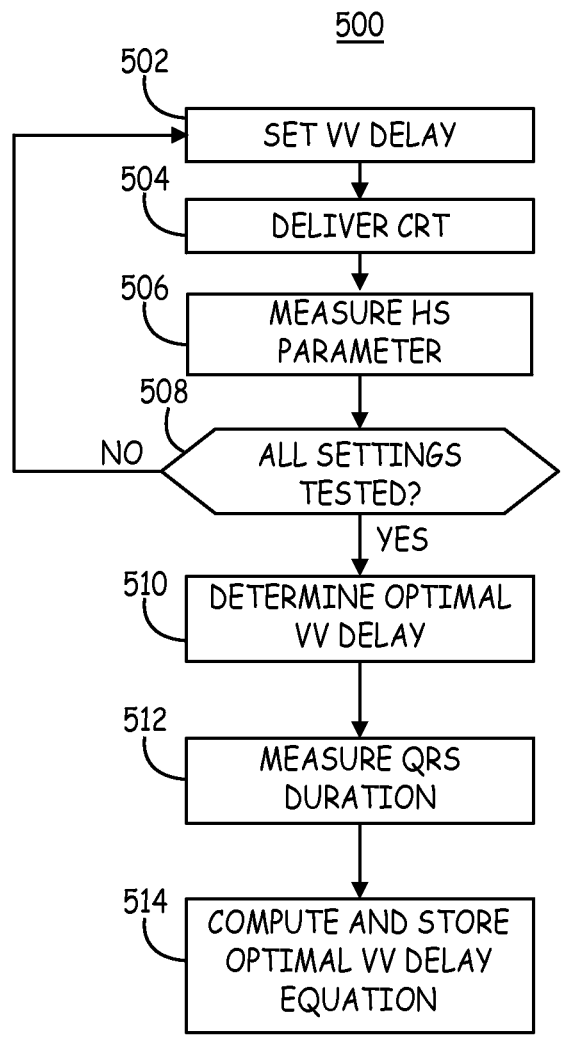
FIG. 6 is a flow chart of a method for setting an optimal VV delay during biventricular pacing according to one embodiment.

FIG. 6 is a flow chart 500 of a method for setting an optimal VV delay during biventricular pacing. In a manner similar to the methods described above, an initial VV delay setting is applied (block 502) during CRT delivery (block 504). A HS parameter is measured (block 506). The HS parameter is measured for multiple VV delay settings until all desired test settings have been applied during CRT delivery as determined at block 508. During application of various VV delay test settings, the AV delay may be set to a value optimized according to the method described in conjunction with FIG. 5.

The HS parameter values measured for various VV delay settings are compared at block 510 to identify the optimal VV delay setting. In various embodiments, a HS parameter measured for optimizing the VV delay may include an S1-S2 interval, QRS-S1 interval, the splitting time between mitral valve component M1 and tricuspid valve component T1 in the S1 sound or the merging of M1 and T1 indicating synchronization of both LV and RV chambers, or a myocardial performance index as mentioned previously herein, or any other parameter or feature derived from the HS signal.

In one embodiment, the conduction parameter measured at block 512 is the A-RVsense interval (which may follow a paced or sensed atrial event). The VV delay is defined as a linear function of the QRS duration in one embodiment. A coefficient K in the equation VV delay=K*(QRS duration)+C may be solved for using the known optimal VV delay determined at block 510, the QRS duration measured at block 512 and a fixed value for intercept C. The coefficient K is stored at block 514 for subsequent use in computing an updated optimal VV delay each time the QRS duration is re-measured, which may be as frequently as every minute in some embodiments.

The coefficient K is also updatable by repeating the HS signal analysis on a periodic basis. The process shown in flow chart 500 may be repeated as often as desired to maintain an optimized patient-specific equation for defining VV delay as a function of the QRS duration using an optimized value for the coefficient K (or intercept C).

Figure 7:
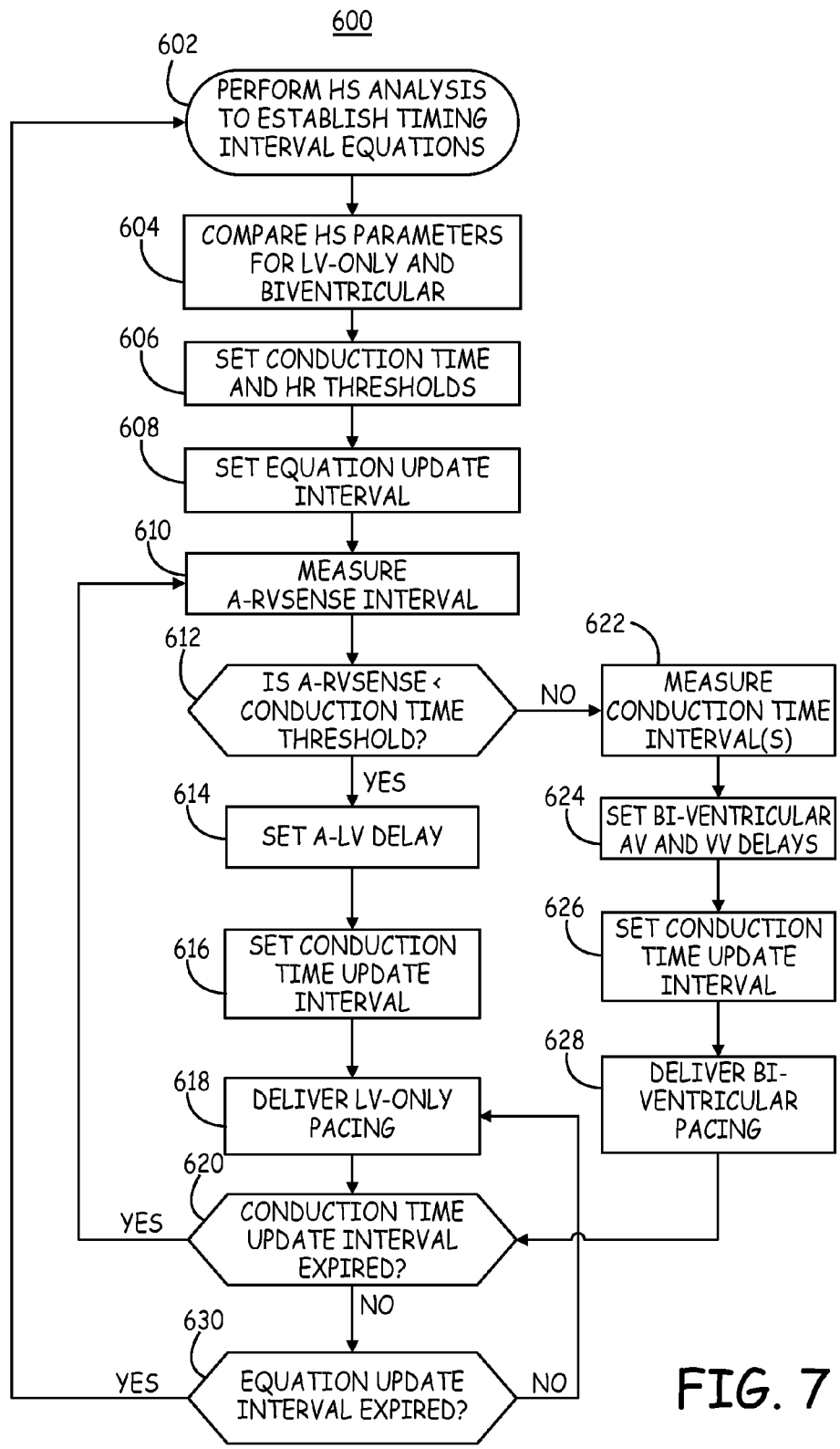
FIG. 7 is a flow chart of a method for controlling adaptive CRT according to one embodiment.

FIG. 7 is a flow chart 600 of a method for controlling adaptive CRT according to one embodiment. At block 602, HS analysis is performed to establish equations defining CRT control parameters as functions of measured conduction times, as described in conjunction with FIGS. 4 through 6. HS analysis is performed to determine an optimal AV delay for use during LV-only pacing. A coefficient or intercept used in an equation to update the AV delay as a function of a measured conduction time interval is stored. Unique coefficients (or intercepts) may be stored corresponding to atrial pacing, atrial sensing and different heart rates.

Similarly, HS analysis is performed to determine an optimal AV and VV delay for use during biventricular pacing. The coefficients (or intercepts) are solved for in respective equations defining the AV delay and the VV delay as functions of respective measured conduction times. Unique coefficients (or intercepts) may be stored corresponding to atrial pacing, atrial sensing and different heart rates.

Once the coefficients and/or intercepts used to define equations for computing optimized CRT timing control parameters are stored for both LV-only and biventricular pacing, the HS parameter(s) measured at the optimal AV delay for LV-only pacing and the HS parameter(s) measured at the optimal AV and VV delay for biventricular pacing may be compared at block 604. This comparison may be made for a resting heart rate only or for multiple heart rate ranges. This comparison is optional but may be performed to identify whether the patient may benefit more from LV-only pacing or from biventricular pacing, even when AV conduction is intact or at differing A-RVsense intervals or heart rates.

A conduction time threshold and a heart rate threshold may be set at block 606 to control when switching between LV-only pacing and biventricular pacing occurs. These thresholds may be set based at least in part on the comparison of the best HS parameter values for LV-only pacing and for biventricular pacing. If a measured AV conduction time is longer than the conduction time threshold, the IMD will switch from LV-only pacing to biventricular pacing until the AV conduction time falls below a switching threshold again (which may be required to be sustained for one or more heart beats). Additionally, a heart rate threshold may be set. In one embodiment, if the A-RVsense conduction time is less than approximately 200 or 250 ms, and the heart rate is less than 100 beats per minute, LV-only pacing is delivered. Otherwise, biventricular pacing is delivered.

The comparison between the HS parameters at optimal settings for each of LV-only and biventricular pacing may be used to adjust the switching thresholds of LV-only and biventricular pacing in some embodiments. If, for example, biventricular pacing results in significantly better hemodynamic performance than LV-only pacing based on the HS analysis, even when intrinsic AV conduction times are normal, the processor may control the therapy delivery module to deliver biventricular pacing all or a majority of the time until the next HS signal analysis is performed. This may be accomplished by adjusting a conduction time threshold and/or heart rate (HR) threshold which control the switching between LV-only and biventricular pacing at block 606. If the AV conduction time threshold is set to a minimum value and/or the HR threshold for switching from biventricular to LV-only pacing is set to a minimum value, biventricular pacing will be delivered most of the time. As long as the AV conduction time is longer than the minimally set threshold and/or the HR is greater than the minimally set HR threshold, biventricular pacing will occur.

In some embodiments, different AV conduction time thresholds may be set for different HR ranges to control whether biventricular pacing or LV-only pacing is delivered for the different HR ranges based on which pacing mode produced the greatest improvement in the measured HS parameter(s) for a given HR range. In other embodiments, in response to superior hemodynamic results during biventricular pacing as compared to LV-only pacing, the processor 80 may fix the pacing mode as a biventricular mode until the next HS signal analysis is performed. The pacing mode will not switch from biventricular to LV-only pacing in response to a change in HR or a change in intrinsic AV conduction time.

In other examples, LV-only pacing may be found to be superior to biventricular pacing even at relatively long intrinsic AV conduction times. As such, in some embodiments, improvement in a HS parameter measured during optimal LV-only pacing as compared to optimal biventricular pacing may result in increasing an AV conduction time threshold and/or increasing a HR threshold that triggers a switch between LV-only and biventricular pacing. This will increase the likelihood of LV-only pacing by increasing the range of AV conduction times and/or range of heart rates for which LV-only pacing is delivered.

In other embodiments, the conduction time threshold and a HR threshold for controlling selection of LV-only and biventricular pacing modes are set without comparing the optimal LV-only and optimal biventricular HS parameter values. A conduction time threshold is set according to a default value, clinician preference, or based on the patient's intrinsic AV conduction time measured at resting HR and/or different HR ranges. Different threshold criteria may be set for switching from LV-only pacing to biventricular pacing than the threshold criteria used for switching from biventricular pacing back to LV-only pacing. A hysteresis effect or different number of proximate cardiac cycles meeting the threshold criteria may be required.

At block 608, a timer controlling an equation update interval is set. This update interval controls when a HS signal analysis is repeated to update the stored coefficient(s) and/or intercepts(s) used to define equations for computing the optimal timing parameter settings. For example, the equation update interval may be set to 24 hours, 48 hours, one week, one month or another desired interval.

At block 610, the AV conduction time is measured for controlling pacing mode. This AV conduction time may be an A-RVsense interval as indicated at block 610. If this A-RVsense interval is less than the previously set conduction time threshold, it is used to compute an optimal A-LV delay at block 614. The previously stored coefficient or intercept defining an equation for A-LV delay as a function of A-RVsense is used. As described above, the equation A-LV delay=K*(A-RVsense)+C is used in one embodiment, wherein K is solved for and stored at block 602 and A-RVsense is the currently measured A-RVsense interval. The intercept C may be a programmable value and may range from approximately +45 ms to −65 ms in one embodiment. An optimal value for C may be determined from linear modeling of data obtained from a population of patients receiving CRT. C may be optimized using echocardiography or other clinical means in some embodiments.

Upper and lower limits may be placed on the A-LV delay to prevent non-physiological or undesirable A-LVpace intervals. For example, in one embodiment, the A-LV delay must not result in a pacing pulse less than 40 ms prior to an RV depolarization. If an A-LV delay is computed using the stored equation that is less than A-RVsense−40 ms, the A-LV delay may be set to a default value equal to A-RVsense−40 ms. An LV pacing pulse delivered less than 40 ms earlier than an R-wave in the RV may result in pseudo-fusion. Pseudo-fusion occurs when the LV pacing pulse evoked response occurs substantially simultaneously with an intrinsic LV depolarization conducted from the RV.

After setting the A-LV delay, which may be set separately for atrial pacing and atrial sensing, a timer controlling a conduction time update interval is set at block 616. The conduction time update interval is the time interval at which measurements of the A-RVsense conduction time are repeated for use in updating the optimal A-LV delay. At block 618, LV-only pacing is delivered using the computed optimal A-LV delay. Upon expiration of the conduction time update interval, as determined at block 620, the process returns to block 610 to measure the A-RVsense interval.

If the A-RVsense interval is still less than the conduction time threshold for LV-only pacing, the A-LV delay is adjusted at block 614 to a value computed using the newly measured A-RVsense interval and the previously stored coefficient (or intercept). LV-only pacing will continue as long as the A-RVsense interval remains below the conduction time threshold (and any other LV-only pacing criteria such as a heart rate criterion are met). The A-LV delay is updated using the stored equation and updated measurements of A-RVsense upon expiration of each scheduled conduction time update interval.

If the equation update interval expires, as determined at block 630, the process returns to block 602 to repeat an analysis of the HS signal. Optimal CRT timing control parameters are identified based on HS signal analysis. The coefficient(s) and/or intercept(s) are solved for in equations defining the control parameters as functions of respective conduction times. The coefficients and/or intercepts are updated and stored at block 602 and the process continues as described above.

If the A-RVsense interval exceeds the conduction time threshold at block 612, the IMD will switch to biventricular pacing and will advance to block 622. If additional conduction time intervals need to be measured besides the A-RVsense interval for computing biventricular pacing timing control parameters, these conduction time intervals are measured at block 622. In one embodiment, the P-wave duration is measured at block 622. The AV delay during biventricular pacing is computed as a function of P-wave duration. Either an A-RV delay or an A-LV delay may be computed using a measured P-wave duration and stored equation. Additionally, the QRS duration is measured at block 622 in one embodiment. The VV delay during biventricular pacing can be computed as a function of the QRS duration and a stored equation.

These P-wave duration and QRS duration measurements are used to compute the optimal biventricular pacing intervals at block 624. In one embodiment, the AV delay is computed according to the equation AV delay=(A-Pend)+offset. A-Pend is the P-wave duration measured at block 622. Offset is an updatable intercept in the linear equation that is solved for during the HS analysis at block 602 and stored in IMD memory until it is updated during the next HS analysis. Alternatively the AV delay may be defined as a function of the measured A-RVsense interval and a coefficient multiplied by the A-RVsense interval or an intercept is solved for during HS signal analysis to establish an equation defining the optimal biventricular AV delay.

In an illustrative embodiment the VV delay used during biventricular pacing is computed according to the equation VV delay=K*QRSduration+C. The updatable coefficient K is stored in IMD memory and updated during each HS signal analysis. C may be a fixed constant stored in IMD memory and may be selected based on modeling performed on a patient population. It is noted that in the various linear equations defining a control parameter, the use of the same letters "K" representing a coefficient value and "C" representing an intercept value is not intended to mean that the different equations for different control parameters have the same coefficient or intercept values; in other words "K" and "C" can be defined uniquely for each control parameter in the generalized equation Y=K*X+C.

A timer controlling the conduction time update interval is set at block 626, and biventricular pacing is delivered at block 628 using the computed timing control parameters. Upon expiration of the conduction time update interval, as determined at block 620, the process may return to block 610 to measure the A-RVsense interval. If the A-RVsense interval is greater than the conduction time threshold for LV-only pacing, the IMD remains in a biventricular pacing mode. Any conduction times needed for computing updated pacing timing control parameters are measured again at block 622, e.g. P-wave duration or QRS duration. Updated AV and VV delays are computed at block 624 using the updated conduction time measurements from block 622.

In some embodiments, the interval at which the A-RVsense interval is measured for controlling switching between biventricular and LV-only pacing may be defined differently than the interval for updating conduction time interval measurements used for computing updated timing control parameters. For example, an A-RVsense interval may be measured every minute for controlling the ventricular pacing mode while the P-wave duration and the QRS duration may be measured every 15 minutes for adjusting the timing control parameters. The methods described herein are not limited to any particular time schedule for updating the various measured conduction time intervals and HS-derived hemodynamic parameters and each measured parameter may have its own update interval.

Upon expiration of the equation update interval, as determined at block 630, the HS signal analysis is repeated at block 602. Any coefficients and/or intercepts used in equations defining CRT timing control parameters as functions of conduction times are updated based on HS parameter optimization. As such, the control parameters can be updated according to a first frequency or rate of conduction time interval measurements. The equation used to compute the control parameters can be updated according to a second frequency of performing heart sound signal analysis. The control parameters may be updated more frequently than the heart sounds signal analysis is performed for updating the equations used to compute the control parameters.

The techniques disclosed herein provide updatable equations for computing a therapy control parameter as a function of a measured cardiac conduction time. Instead of requiring a full hemodynamic signal analysis to identify an optimal control parameter each time the control parameter is adjusted, the patient-specific optimized equation is stored and the control parameter is periodically updated using only the stored equation and updated conduction time measurements without performing additional hemodynamic measurements. Furthermore, instead of a using a fixed equation for updating the control parameter only in response to new measurements of the cardiac conduction time, the equation itself is also updatable. The equation is periodically updated by solving for coefficients or intercepts defining the equation when hemodynamic signal analysis is performed to identify a hemodynamically optimized control parameter value. During periods of time between updating the equation, the control parameter is adjusted using only the stored equation and updated measurements of the conduction time parameter defining the equation.

While particular examples of timing parameters and equations defining the timing parameters are provided herein pertaining to CRT, it is recognized that any therapy control parameter used for controlling a therapy delivered to the heart may be optimized using the techniques described herein. Furthermore, determining a patient-specific equation for defining a control parameter as a function of a measured conduction time may be performed in conjunction with other physiological sensor signals in addition to or instead of a HS sensor signal. Any signal correlated to hemodynamic function of the heart may be useful in determining and updating coefficients and intercepts defining an equation for computing an optimal pacing control parameter as a function of a cardiac conduction time.

The techniques and flow charts presented herein may be combined in various embodiments and are not limited to the particular number or order of steps described herein. It is recognized that operations may be performed in a different order and some operations may be added or removed without departing from the gist of the disclosed techniques.

Thus, a medical device and associated methods for controlling and delivering a pacing therapy have been presented in the foregoing description with reference to specific embodiments. It is appreciated that various modifications to the referenced embodiments may be made without departing from the scope of the disclosure as set forth in the following claims.

The invention claimed is:

1. A method, comprising:
sensing a first cardiac signal comprising first events corresponding to cardiac electrical events;
sensing a second cardiac signal comprising second events corresponding to cardiac hemodynamic events; and
enabling a processor to:
measure a cardiac conduction time interval using the first cardiac signal,
control a signal generator to deliver a pacing therapy and adjust a first pacing control parameter to a plurality of settings during the pacing therapy delivery,
measure a hemodynamic parameter value from the second cardiac signal corresponding to each of the plurality of settings,
identify an optimal setting from the plurality of settings in response to the measured hemodynamic parameter values,
use the identified optimal setting and the measured cardiac conduction time interval to solve for a first patient-specific equation configured to be used to adjust the first pacing control parameter based on cardiac conduction time interval, the first patient-specific equation defining the first pacing control parameter as a function of the cardiac conduction time interval, and
use the first patient-specific equation to compute a setting for the first pacing control parameter based on the cardiac conduction time interval.

2. The method of claim 1, wherein solving for the first patient-specific equation comprises computing a patient-specific value of at least one of a coefficient and an intercept.

3. The method of claim 1, further comprising enabling a processor to:
repeat measurement of the cardiac conduction time interval to obtain an updated conduction time interval; and
use the first patient-specific equation to compute an updated setting for the first pacing control parameter based on the updated cardiac conduction time interval.

4. The method of claim 1, further comprising enabling a processor to:
set a first time interval for updating the first patient-specific equation;
upon expiration of the first time interval, repeat measuring the hemodynamic parameter value from the second cardiac signal corresponding to each of the plurality of settings and identifying an updated optimal setting from the plurality of settings in response to the measured hemodynamic parameter values; and
use the identified updated optimal setting to solve for an updated first patient-specific equation.

5. The method of claim 4, further comprising enabling a processor to:
- set a second time interval for updating the cardiac conduction time interval measurement, the second time interval different than the first time interval; and
- upon expiration of the second time interval, repeat measurement of the cardiac conduction time interval to obtain an updated cardiac conduction time interval and use the updated first patient-specific equation to compute an updated setting for the first pacing control parameter based on the updated conduction time interval.

6. The method of claim 1, further comprising enabling the processor:
- use an identified optimal setting of a second pacing control parameter identified in response to the second cardiac signal and the measured cardiac conduction time interval to solve for a second patient-specific equation configured to be used to adjust the second pacing control parameter based on cardiac conduction time interval, the second patient-specific equation defining the second pacing control parameter as a function of the cardiac conduction time interval;
- control the signal generator to selectively deliver the pacing therapy in one of a first pacing mode and a second pacing mode in response to the first cardiac signal;
- use the first patient-specific equation to compute an optimal setting for the first pacing control parameter in response to selectively delivering pacing according to the first pacing mode; and
- use the second patient-specific equation to compute an optimal setting for the second pacing control parameter in response to selectively delivering pacing according to the second pacing mode.

7. The method of claim 6, wherein the first and second pacing modes comprise a single ventricle pacing mode and a biventricular pacing mode, respectively, the first pacing control parameter comprising an atrial-ventricular delay and the second pacing control parameter comprising a ventricular-ventricular delay.

8. The method of claim 1, wherein the hemodynamic signal comprises a heart sound signal.

9. The method of claim 1, wherein the second events comprise systolic events, the hemodynamic parameter value measured using a systolic event.

10. The method of claim 1, wherein the second events comprise diastolic hemodynamic events, the hemodynamic parameter value measured using a diastolic hemodynamic event.

11. The method of claim 1, wherein the therapy comprises cardiac resynchronization therapy.

12. The method of claim 1, wherein solving for the first patient-specific equation comprises:
- computing a patient-specific value of one of a coefficient and an intercept at a first time point;
- repeating measuring the hemodynamic parameter value from the second cardiac signal corresponding to each of the plurality of settings at a second time point later than the first time point;
- identifying a second optimal setting from the plurality of settings in response to the measured hemodynamic parameter values at the second time point; and
- computing a patient-specific value of the other of the coefficient and the intercept using the second optimal setting.

13. The method of claim 1 wherein the first patient-specific equation comprises $$Y = K*X + C$$

wherein Y is a timing parameter setting, K is a coefficient, X is the measured conduction time interval, and C is an intercept.

14. The method of claim 1, wherein the first pacing control parameter is configured to be updated according to a first frequency.

15. The method of claim 1, wherein the first pacing control parameter is configured to be updated according to a rate of cardiac conduction time interval measurement.

16. The method of claim 1 wherein the patient-specific equation is configured to be updated according to a second frequency of performing heart sound signal analysis.

17. A medical device for controlling and delivering a cardiac pacing therapy, the device comprising:
- a plurality of electrodes for sensing a first cardiac signal comprising first events corresponding to cardiac electrical events;
- a physiological sensor for sensing a second cardiac signal comprising second events corresponding to cardiac hemodynamic events;
- a signal generator for delivering a pacing therapy to a patient's heart via the plurality of electrodes; and
- a processor to:
  - measure a cardiac conduction time interval using the first cardiac signal,
  - control the signal generator to deliver a pacing therapy and adjust a first pacing control parameter to a plurality of settings during the pacing therapy delivery,
  - measure a hemodynamic parameter value from the second cardiac signal corresponding to each of the plurality of settings,
  - identify an optimal setting from the plurality of settings in response to the measured hemodynamic parameter values,
  - uses the identified optimal setting and the measured cardiac conduction time interval to solve for a first patient-specific equation configured to be used to adjust the first pacing control parameter based on cardiac conduction time interval, the first patient-specific equation defining the first pacing control parameter as a function of the cardiac conduction time interval, and
  - use the first patient-specific equation to compute a setting for the first pacing control parameter based on the cardiac conduction time interval.

18. The device of claim 17, wherein solving for the first patient-specific equation comprises computing a patient-specific value of at least one of a coefficient and an intercept.

19. The device of claim 17, wherein the processor is further configured to:
- repeat measuring the cardiac conduction time interval to obtain an updated cardiac conduction time interval; and
- use the first patient-specific equation to compute an updated setting for the first pacing control parameter based on the updated cardiac conduction time interval.

20. The device of claim 17, wherein the processor is further configured to:
- set a first time interval for updating the first patient-specific equation;
- upon expiration of the first time interval, repeat measuring the hemodynamic parameter value from the second cardiac signal corresponding to each of the plurality of settings and identifying an updated optimal setting from the plurality of settings in response to the measured hemodynamic parameter values; and use the updated optimal setting to solve for an updated first patient-specific equation.

21. The device of claim 20, wherein the processor is further configured to:
set a second time interval for updating the cardiac conduction time interval measurement, the second time interval different than the first time interval; and
upon expiration of the second time interval, repeat measurement of the cardiac conduction time interval to obtain an updated cardiac conduction time interval and use the updated first patient-specific equation to compute an updated setting for the first pacing control parameter based on the updated conduction time interval.

22. The device of claim 17, wherein the processor is further configured to:
use an identified optimal setting of a second pacing control parameter and the measured cardiac conduction time interval to solve for a second patient-specific equation configured to be used to adjust the second pacing control parameter based on cardiac conduction time interval, the second patient-specific equation defining the second pacing control parameter as a function of the cardiac conduction time interval;
control the signal generator to selectively deliver the pacing therapy in one of a first pacing mode and a second pacing mode in response to the first cardiac signal;
use the first patient-specific equation to compute an optimal setting the first pacing control parameter in response to selectively delivering pacing according to the first pacing mode; and
use the second patient-specific equation to compute an optimal setting for the second pacing control parameter in response to selectively delivering pacing according to the second pacing mode.

23. The device of claim 22, wherein the first and second pacing modes comprise a single ventricle pacing mode and a biventricular pacing mode, respectively, the first pacing control parameter comprising an atrial-ventricular delay and the second pacing control parameter comprising a ventricular-ventricular delay.

24. The device of claim 17, wherein the hemodynamic signal comprises a heart sound signal.

25. The device of claim 17, wherein the second events comprise systolic events, the hemodynamic parameter value measured using a systolic event.

26. The device of claim 17, wherein the second events comprise diastolic events, the hemodynamic parameter value measured using a diastolic event.

27. The device of claim 17, wherein the pacing therapy comprises cardiac resynchronization therapy.

28. The device of claim 17, wherein solving for the first patient-specific equation comprises:
computing a patient-specific value of one of a coefficient and an intercept at a first time point;
repeating measuring the hemodynamic parameter value from the second cardiac signal corresponding to each of the plurality of settings at a second time point later than the first time point;
identifying a second optimal setting from the plurality of settings in response to the measured hemodynamic parameter values at the second time point; and
computing a patient-specific value of the other of the coefficient and the intercept using the second optimal setting.

29. A non-transitory computer-readable medium storing instructions which cause a medical device to perform a method for controlling a cardiac pacing therapy, the method comprising:
sensing a first cardiac signal comprising first events corresponding to cardiac electrical events;
sensing a second cardiac signal comprising second events corresponding to cardiac hemodynamic events;
measuring a cardiac conduction time interval using the first cardiac signal;
controlling a signal generator to deliver a pacing therapy and adjust a first pacing control parameter to a plurality of settings during the pacing therapy delivery;
measuring a hemodynamic parameter value from the second cardiac signal corresponding to each of the plurality of settings;
identifying an optimal setting from the plurality of settings in response to the measured hemodynamic parameter values;
using the identified optimal setting and the measured cardiac conduction time interval to solve for a first patient-specific equation configured to be used to adjust the first pacing control parameter based on cardiac conduction time interval, the first patient-specific equation defining the first pacing control parameter as a function of the cardiac conduction time interval; and
using the first patient-specific equation to compute a setting for the first pacing control parameter based on the cardiac conduction time interval.

30. A method, comprising:
sensing a first cardiac signal comprising first events corresponding to cardiac electrical events;
sensing a second cardiac signal comprising second events corresponding to cardiac hemodynamic events; and
enabling a processor to:
measure a cardiac conduction time interval using the first cardiac signal, cardiac conduction time interval being one of an AV conduction time interval, a P-wave duration, and a QRS duration,
control a signal generator to deliver a pacing therapy and adjust a first pacing control parameter to a plurality of settings during the pacing therapy delivery,
measure a hemodynamic parameter value from the second cardiac signal corresponding to each of the plurality of settings,
identify an optimal setting from the plurality of settings in response to the measured hemodynamic parameter values,
use the identified optimal setting and the measured cardiac conduction time interval to solve for a first patient-specific equation configured to be used to adjust the first pacing control parameter based on cardiac conduction time interval, the first patient-specific equation defining the first pacing control parameter as a function of the cardiac conduction time interval,
use the first patient-specific equation to compute a setting for the first pacing control parameter based on the cardiac conduction time interval,
repeat measuring the cardiac conduction time interval to obtain an updated conduction time interval, and
in response to obtaining the updated cardiac conduction time interval use the first patient-specific equation to compute an updated setting for the first pacing control parameter based on the updated conduction time interval.

31. The method of claim 30, wherein solving for the first patient-specific equation comprises computing a patient-specific value of a coefficient.

32. The method of claim 30, wherein solving for the first patient-specific equation comprises computing a patient-specific value of an intercept.

* * * * *